United States Patent
Zhang et al.

(10) Patent No.: US 9,697,740 B2
(45) Date of Patent: Jul. 4, 2017

(54) WELLNESS MANAGEMENT METHOD AND SYSTEM BY WELLNESS MODE BASED ON CONTEXT-AWARENESS PLATFORM ON SMARTPHONE

(71) Applicant: Futurewei Technologies Inc., Plano, TX (US)

(72) Inventors: Jianyu Zhang, San Jose, CA (US); Chia Chin Chong, Santa Clara, CA (US)

(73) Assignee: Futurewei Technologies, Inc., Plano, TX (US)

( * ) Notice: Subject to any disclaimer, the term of this patent is extended or adjusted under 35 U.S.C. 154(b) by 56 days.

(21) Appl. No.: 14/468,298

(22) Filed: Aug. 25, 2014

(65) Prior Publication Data

US 2015/0056589 A1    Feb. 26, 2015

Related U.S. Application Data (60) Provisional application No. 61/869,525, filed on Aug. 23, 2013, provisional application No. 61/883,904, filed on Sep. 27, 2013.

(51) Int. Cl.
    *A63B 24/00*    (2006.01)
    *G09B 19/00*    (2006.01)
    *G06F 19/00*    (2011.01)
(52) U.S. Cl.
    CPC ......... *G09B 19/00* (2013.01); *G06F 19/3481* (2013.01); *G09B 19/003* (2013.01)

(58) Field of Classification Search
    CPC ... A63B 24/00; A63B 24/0062; A63B 69/004; G09B 19/00; G09B 19/003; G09B 19/3481; G09F 19/3406
    See application file for complete search history.

(56) References Cited

U.S. PATENT DOCUMENTS

| | | |
|---|---|---|
| 5,067,710 A | 11/1991 | Watterson et al. |
| 9,421,420 B2 | 8/2016 | Zhang et al. |
| 2006/0040793 A1 | 2/2006 | Martens |
| 2006/0205564 A1 | 9/2006 | Peterson |
| 2007/0219059 A1 | 9/2007 | Schwartz et al. |
| 2010/0056340 A1* | 3/2010 | Ellis ............... A61B 5/1038 482/4 |

(Continued)

OTHER PUBLICATIONS

"U.S. Appl. No. 14/500,842, Ex Parte Quayle Action mailed Feb. 1, 2016", 5 pgs.

(Continued)

*Primary Examiner* — Glenn Richman
(74) *Attorney, Agent, or Firm* — Schwegman Lundberg & Woessner, P.A.

(57) ABSTRACT

A device, method and system processes data about the user for determining and recommending a health/wellness action to the user. The action determined can be based on: (1) current biometric and/or motion data about the user (from the sensors), and (2) current health/medical information or condition about the user (from the user's personal information, e.g., health library or programmed into the smartphone). Specific information about the user is taken into consideration when recommending user action, such as the user's specific health or medical conditions.

7 Claims, 3 Drawing Sheets

(56) References Cited

U.S. PATENT DOCUMENTS

| | | |
|---|---|---|
| 2011/0172060 A1* | 7/2011 | Morales ............... A63B 69/004 482/8 |
| 2011/0251021 A1 | 10/2011 | Zavadsky et al. |
| 2011/0281687 A1* | 11/2011 | Gilley ................. G06F 19/3406 482/8 |
| 2012/0313776 A1 | 12/2012 | Utter, II |
| 2013/0013331 A1 | 1/2013 | Horseman |
| 2013/0194066 A1 | 8/2013 | Rahman et al. |
| 2015/0087478 A1 | 3/2015 | Zhang et al. |
| 2016/0007885 A1 | 1/2016 | Basta et al. |
| 2016/0354637 A1 | 12/2016 | Zhang et al. |

OTHER PUBLICATIONS

"U.S. Appl. No. 14/500,842, Notice of Allowance mailed Apr. 22, 2016", 5 pgs.

"U.S. Appl. No. 14/500,842, Response filed Oct. 27, 2015 to Restriction Requirement mailed Oct. 15, 2015", 2 pgs.

"U.S. Appl. No. 14/500,842, Restriction Requirement mailed Oct. 15, 2015", 6 pgs.

"U.S. Appl. No. 15/239,629, Non Final Office Action mailed Sep. 21, 2016", 5 pgs.

* cited by examiner

WELLNESS MANAGEMENT METHOD AND SYSTEM BY WELLNESS MODE BASED ON CONTEXT-AWARENESS PLATFORM ON SMARTPHONE

CROSS-REFERENCE TO RELATED APPLICATIONS

The present application claims priority to U.S. provisional patent Application No. 61/869,525 filed on Aug. 23, 2013 and U.S. provisional patent Application No. 61/883,904 filed on Sep. 27, 2013, both of which are incorporated herein by reference.

TECHNICAL FIELD

The present disclosure relates generally to health and wellness, and more particularly to a method and system for wellness management based on a context awareness platform on a mobile electronic device, such as a smartphone.

BACKGROUND

Health and wellness are becoming more and more important as individuals devote more time to generally non-physical activities, such as work at an office or on a computer. Because a person often performs these activities with little or no physical exertion, such activities are generally bad for a person's overall health and wellness. Similarly, when an individual does engage in some form of physical activity that requires physical exertion, oftentimes the individual overexerts themselves. Such activities are also generally bad for a person's overall health and wellness.

Various activities recommendation systems/services exist in the marketplace—which recommend or remind a person to engage in some physical activity or exercise for physical fitness. However, these systems/services do not ascertain, determine or recognize automatically the person's current physical situations (or capabilities), health/medical conditions and most recent activity history, generate a recommendation for health/wellness, and notify the person. Further, such systems are not capable of being disabled when desirable in some scenarios, such as when the person is attending a meeting. One prior art system is a simple alarm tool. These must be set up manually by the user and do not take into consideration the user's physical situation or past physical activity history.

More particularly, none of the activity recommendations systems/services automatically recommend wellness activities to a user based on the user's physical motion sensed or determined (or inferred) from sensors (e.g., motion sensors) or based on the user's biological state sensed or determined (or inferred) from sensors (e.g., biometric sensors) using a mobile smartphone or other mobile device, where the sensors may be co-located within the mobile device or located on the person and communicatively coupled to the mobile device.

SUMMARY

In one embodiment, there is provided a method for recommending an action to a user for enhancing wellness or health of the user. The method includes receiving first data from a first sensor configured to sense motion of a user and receiving second data from a second sensor configured to sense biometric data of the user. The received first and second data is processed and a type of activity engaged in by the user is identified. A recommended action to be performed by the user is determined in response to the identified type of activity and a current health/medical condition of the user.

In another embodiment, there is provided a mobile wearable device for sensing one or more physical attributes of a user associated with the device and recommending an activity to the user for enhancing wellness of the user. The device includes a processor and one or more sensors configured to sense one or more physical attributes of the associated user and output physical attribute information. The processor is configured to: receive the physical attribute information, identify the user's type of activity based on the received physical attribute information, determine a recommended action to be performed by the user in response to the identified type of activity, and notify the user of the recommended action.

BRIEF DESCRIPTION OF THE DRAWINGS

For a more complete understanding of the present disclosure, and the advantages thereof, reference is now made to the following descriptions taken in conjunction with the accompanying drawings, wherein like numbers designate like objects, and in which.

DETAILED DESCRIPTION

The present disclosure describes a method and system for reminding/recommending/notifying a user to perform some physical activities (e.g., moving, walking, running, etc.) after being generally stationary for a period of time (an "activity reminder"). The present disclosure also describes a method and system for recommending/notifying ("activity recommendation") a user to modify the physical activity(ies) the user is currently engaged in (an "activity recommendation"), such as when the user is physically over/under exerting. For example, when the user is running and the system detects the user's heartbeat is too fast or body temperature is too high, the disclosed system may recommend/notify the user to slow down or stop for a period of time. These systems and methods will assist the user in improving his/her wellness and health.

The present disclosure also describes a method and system that process data about the user, and determines and recommends a health/wellness action to a user. In one embodiment, the action is determined based on: (1) current biometric and/or motion data about the user (from the sensors), and (2) current health/medical information or condition about the user (from the user's personal information, e.g., health library or programmed into the smartphone). Other prior art systems appear limited to recommending "some" physical activity simply for "physical fitness" purposes, in general. These physical fitness activities are general in nature (cardiovascular, exercise, lifting weights, reducing inactivity, etc.) and are simply intended to increase physical strength and/or stamina. The present disclosure also takes into consideration specific information about the user when recommending user action, such as the user's specific health or medical conditions when making a recommendation.

In addition, in another embodiment, the present disclosure may recommend user action that is not directly related to improving the user's physical strength, etc. Instead, that action recommended may be to reduce physical activity in order to alleviate or reduce health risks associated with the user's current medical/health situation. The presence of a medical condition/health specific to the user may also result in different recommend user actions other than simply "more physical activity." Examples of recommended actions may be: call the doctor, take more vitamins, reduce physical activity, make more frequent trips to the bathroom, drink more fluids, consume more/less sugar, etc. This may be one path to help distinguish.

In addition, another embodiment of the present disclosure ascertains and utilizes general health rules (from health industry and knowledge) to assist in recommending an action that reduces the current health risk to the user based on the patient's current situation and current activity(ies).

In other embodiments, the system automatically generates the activity reminder or activity recommendation based on the user's current physical activity and physical attribute(s), and may further be based on recent historical physical activity and attribute(s). Information about the user's physical activity is based on data collected from one or more motion sensors (e.g., accelerometers, gyroscopes, position or location sensors, pressure sensors, etc.), while information about the user's physical attribute(s) is based on data collected from one or more biometric sensors (e.g., a sensor configured to detect a biometric parameter). A biometric parameter is any biological phenomenon exhibited by a person, body or a surrounding environment. In one embodiment, the sensors may be embedded in mobile device (e.g., a smartphone) carried by the user. In another embodiment, the sensors may be physically separate from the mobile device, but physically attached or affixed to the user's body, and further in communication with the mobile device. Another embodiment may provide for a combination thereof.

The activity reminder and recommendation systems and methods may include a learning system for improving accuracy in the identification of the physical activity(ies) engaged in and what activity is recommended to be performed. In addition, if a user is required to be in a stationary mode for a period of time longer than a predetermined reminder threshold (e.g., in a meeting), the system may be overridden and disabled manually by the user or automatically. For example, in the event the user is in a meeting, the system can detect this situation (e.g., by the user's calendar, by the user's location, etc.) and automatically disable or override the system or reminder. In addition, the function of a wellness mode can be disabled or enabled by a user manually.

The systems described herein includes a sensor fusion platform which collects raw data from the sensors (motion and/or biometric—as described above). The raw data is processed and the system determines or infers the user is engaging in certain physical (or generally non-physical) activity or activities. With this data, the user's physical activity can be determined and classified physical activity categories, such as sitting, walking, running, driving, etc. These may be referred to herein as a "motion identifier" or "activity identifier." In addition, different biological states of the user (physical attributes) can be determined and classified into biological state categories, such as perspiration level, heartbeat, body temperature, etc. These may be referred to herein as a "biometric identifier" or "biological state identifier."

The system also includes a context awareness platform for receiving as input the motion and biometric identifiers and automatically generates a "recommended action." This recommended action may include an activity reminder and/or an activity recommendation (as described above).

One benefit of the methods and systems described herein is to provide an automatic reminder/recommendation to the user to engage in or perform some physical activities after being in a relatively stationary mode for an extended period of time. Another benefit is to provide an automatic recommendation/notification to the user to modify his or her current physical activity in the event the user is over/under exerting himself or herself, or to perform some recommended action due to the user's specific medical/health condition coupled with the user's current biometric/motion situation. This will help the user improve his/her wellness and health.

Figure 1:
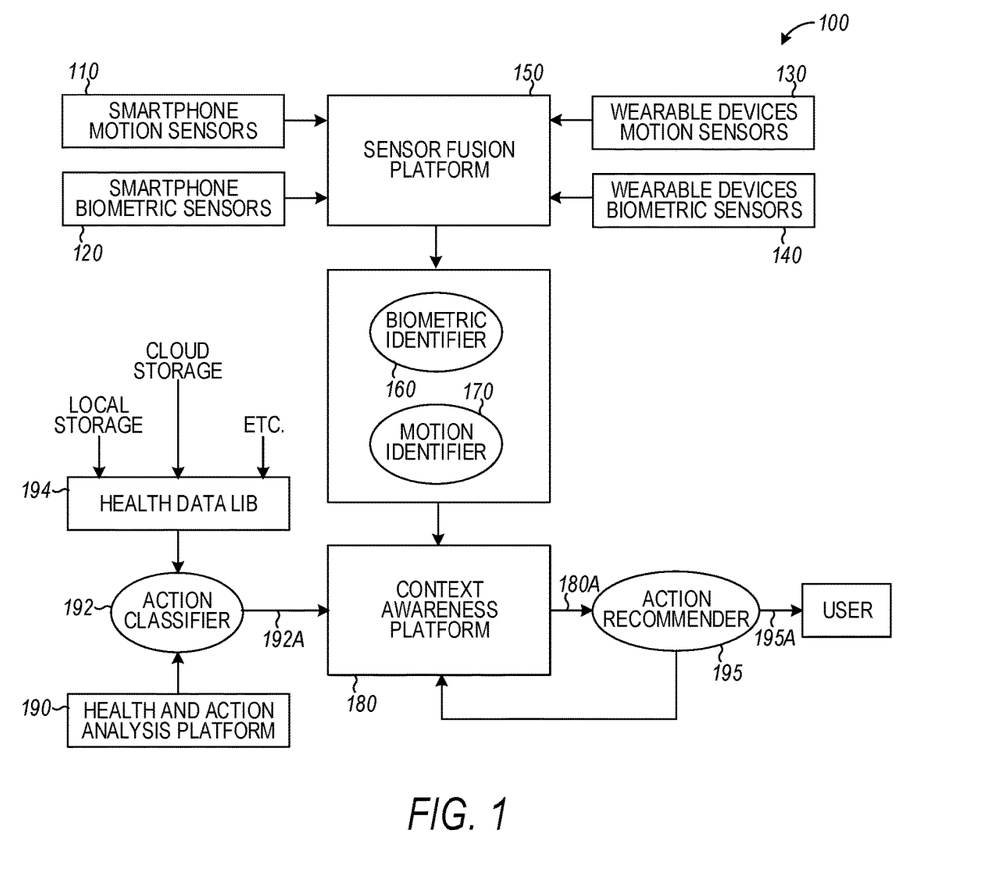
FIG. 1 illustrates a system for wellness management based on a context awareness platform or process within a mobile electronic device in accordance with the present disclosure.

Now turning to FIG. 1, there is illustrated a block diagram of a physical activity recommendation system 100 in accordance with the present disclosure. In this example embodiment, the system 100 includes one or more motion sensors 110 associated with a mobile electronic device (e.g., smartphone), one or more biometric sensors 120 associated with a mobile device (e.g., the smartphone), one or more motion sensors 130 associated with a wearable device and one or more biometric sensors 140 associated with (the same or a different) wearable device. As will be appreciated, although multiple sensors are shown, the system 100 may include a different number of sensors, and the sensors may be associated with the mobile electronic device only, the wearable device only or in any combination thereof.

The system 100 further includes a sensor fusion platform or process 150 that receives biometric and/or motion data from one or more of the sensors 110, 120, 130, 140 and analyzes and processes the received data to classify or generate a biometric identifier 160 and/or a motion identifier 170. The generated biometric identifier 160 and motion identifier 170 are input to a context awareness platform or process 180.

The context awareness platform or process 180 also receives as an input an "action-health list" or "good action list" 192a from an action classifier process 192 relating to different physical activities. The action classifier process 192 receives personal user health information and common health rules from a health and action analysis platform or process 190. The action classifier 192 uses known health information about the user (this may be obtained from external sources and databases, such as the user's health data library 194) and common health rules to generate the good action list. The user's health data library 194 includes the user's personal health data, such as whether the user has high blood pressure, etc. The health and action analysis platform 190 obtains health research and medical information from various sources relating to common health rules, such as a person with high blood pressure should also have a high heart rate.

Based on the common health/medical rules from platform 190 and the user's personal health data from the health library 194 (collectively, health/medical information), the action classifier process 192 generates the good action list 192a for the user. For example, the good action list 192a may include the following items in the list: the user should reduce activity to keep his/her heart rate under a predetermined threshold (e.g., 150/min). Therefore, reducing activity is a good healthy action when the user's heart rate is higher than 150/min. As will be appreciated, there may exist many common health rules and various personal health data for processing, and the action classifier process 192 may generate multiple good action list items. Persons of ordinary skill in the art will understand that various suitable common health rules and different types of personal health data may be input and utilized in the system to generate different good action list items.

It will be appreciated that the good action list 192*a* may be generated initially based on current personal health data and current common health rules available. This process 192 is performed dynamically, but may not necessarily be performed on an hourly or even daily basis—as a person's personal health data usually does not change that often. For example, the good action list could be generated and updated periodically, such as every week or month. Also, the entire list may be re-generated, or only particular items in the current list may be updated. Additionally, the process 192 may be performed upon start-up of the system, and the good action list items will be stored in memory. Alternatively, the good action list items could be generated remotely and pre-stored in memory, and then updated periodically.

With these data inputs (e.g., user's good action list 192*a*, motion identifier(s) 170 and biometric identifier(s) 160), the context awareness platform 180 processes the data and performs a mapping between the biometric identifier(s) 160 and/or motion identifier(s) 170 and the good action list 192*a* in order to generate a list of possible actions 180*a* based on activities and conditions. The following provides two examples of actions for the user (based on activities and conditions):

[IF] user heart rate is higher than 150/min and is exercising, [THEN] recommend that user reduce activity; or

[IF] user heart rate is higher than 150/min and is not exercising, [THEN] recommend that user call doctor.

With the user's current biometric identifier(s) 160 and motion identifier(s) 170, an action recommender process 195 consults the list of actions and determines what activity(ies) or action(s) 195*a* should be recommended to the user. For example, assuming the user's current motion identifier 170 indicates "running" (or exercise) and the current biometric identifier 160 indicates heart rate equal to 160, the action recommender process 195 maps or compares the user's current motion/biometric data against the list of good actions and determines a recommended activity or action.

Once determined, the recommended user action 195*a* is automatically delivered to the user (e.g., through an I/O device in the mobile device, such as a display or speaker). As will be appreciated, multiple biometric identifiers and motion identifiers may be factors in determining a recommended user action. In addition, more than one user action may be recommended.

In one embodiment, the platforms or processes 150, 180, 190, 192 and 195 are included within or performed by the mobile electronic device including the sensors 110, 120. As will be appreciated, the mobile electronic device includes a processor or processing system, memory, various input/output devices, including for communication (wireless, wired) with any external motion sensors, such as motion sensors 130, 140, and a display. One or more software application programs (software, firmware, code) are utilized to perform the actions or provide the functions of the platforms or processes 150, 180, 190, 192 and 195 described herein.

In another embodiment, all or part of the platforms and processes 190 and 192 may reside in a server-type processing device or system physically separate from the mobile device, and the mobile device transmits the sensor data to the server-type processing device. This transmission may be done by communications via wireline, wireless or combination thereof. In yet other embodiments, one or more of the platforms or processes may be incorporated within the mobile electronic device and one or more may reside external to the device.

Figure 2:
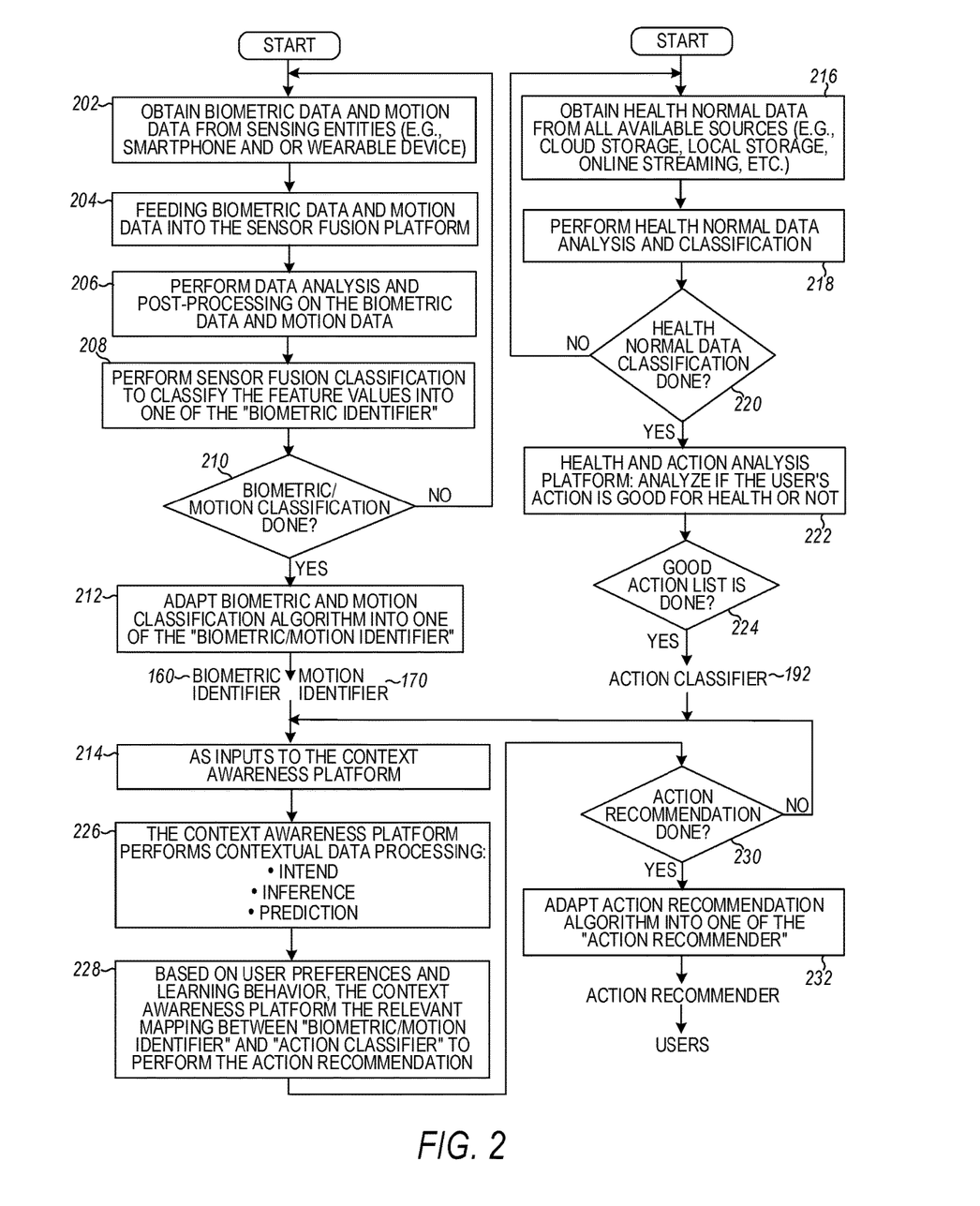
FIG. 2 illustrates a flowchart of a process in accordance with disclosed embodiments that may be performed by the system of FIG. 1.

FIG. 2 illustrates a flowchart of a process 200 in accordance with disclosed embodiments performed by the system 100 of FIG. 1.

The system 100 obtains biometric data and motion data from one or more sensing entities (step 202). For example, the system 100 may obtain the biometric data and the motion data from one or more of the sensors 110, 120, 130, 140. The terms "obtain" or "obtaining" as used herein, can include loading from a storage device, receiving from another device or process, receiving via an interaction with a user, and are not limited to any specific method or way, unless expressly stated.

The system 100 inputs the raw biometric data and the raw motion data into the sensor fusion platform or process 150 (step 204). For example, the sensor fusion platform 150 receives biometric and/or motion data generated from the one or more of the sensors 110, 120, 130, 140.

The sensor platform 150 performs data analysis and post-processing on the biometric data and the motion data (step 206) to categorize the user's current activity/condition. This may include a sensor classification operation to classify the sensor data into one or more biometric identifiers and/or motion identifiers (step 208). For example, the sensor platform 150 analyzes and processes the received sensor data to classify or generate the user's current biometric identifier(s) 160 and/or the motion identifier(s) 170. For example, motion identifiers 170 may identify the motion as sleeping, sitting walking, running, driving, etc. Examples of biometric identifiers 160 may include heart rate, body temperature, respiratory rate, etc. More than one type of activity may be determined or identified. As will be appreciated, various methods and processes are known to those of ordinary skill in the art for determining the type of activity based on motion sensor data and/or biometric sensor data. Though a few examples are described, different and additional motion identifiers and biometric identifiers can be determined and used in the system 100.

A determination of whether biometric and/or motion classification is complete is made (step 210). For example, the acquisition of the sensor data and determination classification may be performed one time or multiple times periodically, and may also be performed over an extended period of time (e.g., second, minute, hours) depending on the desired application and likely activities. The frequency and timing of the sensor data acquisition and identifier determination may be based on the user's current health data (e.g., what health conditions the user may have). If incomplete, the process reverts to step 202. If complete, then a biometric and motion classification process results in the generation of the one or more biometric identifiers 160 and/or the motion identifiers 170 (step 212). The generated biometric identifier(s) 160 and motion identifier(s) 170 are input to the context awareness platform 180 along with the good action list 192*a* (step 214) and further processed.

The good action list 192*a* is generated from known health normal information about various physical activities and user-specific health information (as described more fully above). For example, the process may obtain the user's health information (step 216) from external sources and databases, such as from the health data library 194 (cloud storage, local storage, online streaming, etc.). In addition, health normal information is obtained from various sources (as described above). Health data analysis and classification is performed (step 218). This step may classify the user into a medical/health category based on various factors. For example, the user may be classified as diabetic, high cholesterol, high blood pressure, or any other medical condition that may affect the user's health or wellness. A determination of whether health data classification is complete is made (step 220). If incomplete, then the process 200 reverts to step 216. If complete, then the health and action analysis platform 190 determines the good action list 192*a* (step 222). The good action list 192*a* is input to the context awareness platform 180.

With the inputs shown, the context awareness platform 180 performs contextual data processing (step 226). Mapping between the received biometric/motion identifier(s) and the good action list 192*a* is performed (step 228). For example, the context awareness platform 180 processes the data (good action list 192*a* and sensor identifiers 160, 170) and generates a mapping between the biometric identifier 160 and/or the motion identifier 170 and the good action list 192*a* to determine an action recommendation. In another embodiment, the system may learn facts or behavior of the user, and the user action(s) recommended may be based at least in part on the user' past or learned behavior.

A determination of whether the action recommendation process is complete is made (step 230). If incomplete, the system reverts to step 214. If complete, the action recommendation process is performed by the action recommender 195 (step 232). The recommended action 195*a* is delivered or notified to the user (e.g., through an I/O device in the mobile device, such as a display or speaker) or some other method of notification using the device.

Figure 3:
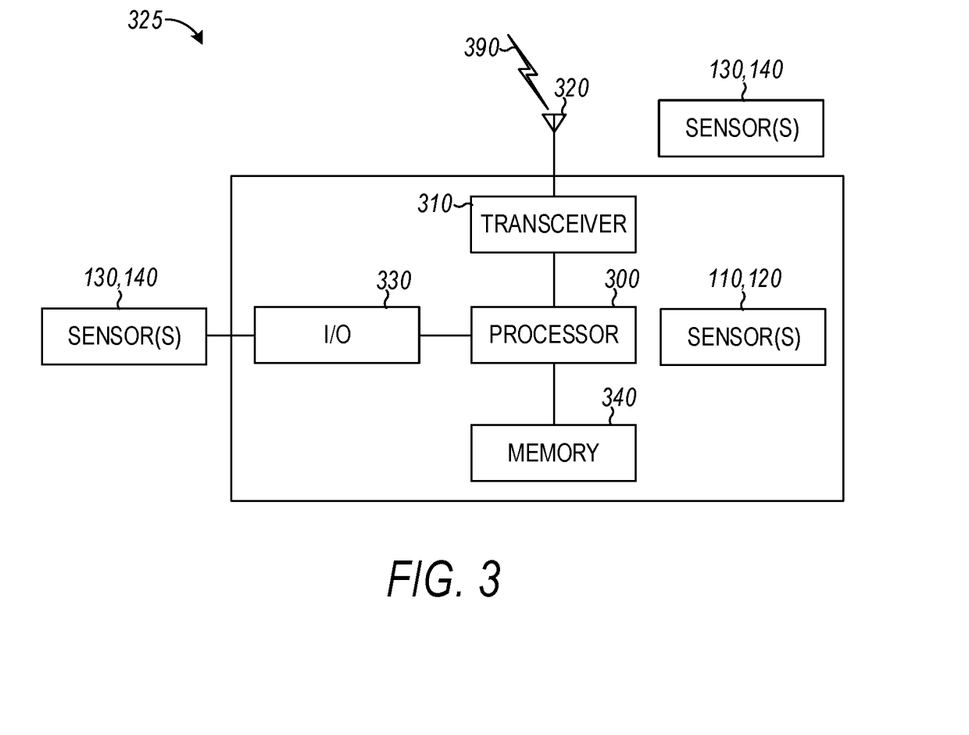
FIG. 3 illustrates an overall block diagram of an example mobile electronic device in accordance with disclosed embodiments.

Turning now to FIG. 3, there is shown an overall block diagram of an example mobile electronic device 325 (e.g., smartphone) implementing the system 100 described herein. As will be appreciated, during operation the mobile electronic device 325 will be carried, worn by or otherwise affixed to the user.

The electronic device 325 includes a processor 300, a transceiver 310, an antenna element 320, one or more input/output devices 330 (e.g., speaker/microphone, keypad, display/touchpad, electrical connectors, etc.), memory 340 and the sensors 110, 120. The sensors 110, 120 are incorporated therein and/or form part of the mobile electronic device 325 and are coupled to the processor 300 (directly or indirectly through other circuitry, such as the I/O devices 330). The sensors 130, 140 are physically external to the electronic device 325 and communicatively coupled to the electronic device 325 via a wired communication connection (e.g., electrical connector) and/or a wireless communication link 390.

The electronic device 325 may include other components, devices or functionalities, though not shown, and may also include fewer or more of the foregoing described elements.

The processor 300 may be a general purpose, special purpose or digital signal processor, and may be a plurality of processors or combination of such processors. The processor 300 includes functionality to perform signal coding, data processing, power control, input/output processing, and/or any other functionality enabling the electronic device 325 to operate in the system 100 and perform all or some of the process 200 including those functions described as being performed by one or more of the platforms or process 150, 180, 190.

The processor 300 is coupled to the transceiver 310 which is coupled to the antenna element 320. It will be understood that the processor 300 and the transceiver 310 may be separate components or integrated together. Similarly, the antenna element 320 may be a single element or a number of elements (multiple antennas or elements).

The processor 300 is also coupled to the one or more input/output devices 330 (including ports, busses, electrical connectors) operable for inputting/outputting data and signals. In addition, the processor 300 is coupled to memory 330 operable for storing and retrieving data, computer code, software, firmware and instructions. Any suitable type of memory storage device may be included, such as random-access memory (RAM), read-only memory (ROM), hard disk, subscriber identity module (SIM) card, a memory stick, a secure digital (SD) memory card, and the like.

In some embodiments, some or all of the functions or process(es) described herein and performed by the mobile electronic device 325 are implemented or supported by a computer program that is formed from computer readable program code and that is embodied in a computer readable medium. The phrase "computer readable program code" includes any type of computer code, including source code, object code, executable code, firmware, software, etc. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The terms "include" and "comprise," as well as derivatives thereof, mean inclusion without limitation. The term "or" is inclusive, meaning and/or. The phrases "associated with" and "associated therewith," as well as derivatives thereof, mean to include, be included within, interconnect with, contain, be contained within, connect to or with, couple to or with, be communicable with, cooperate with, interleave, juxtapose, be proximate to, be bound to or with, have, have a property of, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A computer-readable storage medium comprising instructions that, when executed by at least one processor of a machine, cause the machine to perform operations for recommending an action to a user for enhancing wellness or health of the user, the operations comprising:

receiving first data from a first sensor configured to sense motion of a user;

receiving second data from a second sensor configured to sense biometric data of the user;

processing the received first and second data and identifying a type of activity engaged in by the user;

determining a recommended action to be performed by the user in response to the identified type of activity and a current health/medical condition of the user; and     notifying the user of the recommended action.

2. The computer-readable storage medium in accordance with claim 1 wherein processing and identifying further comprises:
 for different time periods, processing received data and identifying a type of activity for each of the different time periods.

3. The computer-readable storage medium in accordance with claim 1 wherein processing and identifying further comprises:
 storing historical activity information for the user.

4. The computer-readable storage medium in accordance with claim 1 wherein the current health/medical condition of the user comprises a medical condition known to the user, the medical condition has associated therewith a health risk and the identified activity will increase the health risk to the user.

5. A mobile wearable device comprising:
 a first sensor configured to sense motion of a user;
 a second sensor configured to sense biometric data of the user; and
 a processor configured to:
  receive first data from the first sensor and receive second data from the second sensor,
  identify the user's type of activity based on the received first data and second data,
  determine a recommended action to be performed by the user in response to the identified type of activity, and
  notify the user of the recommended action.

6. The device in accordance with claim 5 wherein the processor is further configured to:
 receive medical condition information about the user identifying a medical condition of the user; and
 determine the recommended action to be performed by the user in response to the identified type of activity and the medical condition of the user.

7. The method in accordance with claim 6 wherein medical condition of the user has associated therewith a health risk and the identified activity will increase the health risk to the user.

* * * * *

UNITED STATES PATENT AND TRADEMARK OFFICE
CERTIFICATE OF CORRECTION

PATENT NO. : 9,697,740 B2
APPLICATION NO. : 14/468298
DATED : July 4, 2017
INVENTOR(S) : Zhang et al.

Page 1 of 1

It is certified that error appears in the above-identified patent and that said Letters Patent is hereby corrected as shown below:

On the Title Page

In item (71), in "Applicant", in Column 1, Line 1, after "Technologies", insert --,--

In the Specification

In Column 8, Line 14, delete "330" and insert --340-- therefor

In the Claims

In Column 10, Line 16, in Claim 7, delete "method" and insert --device-- therefor Signed and Sealed this
Thirtieth Day of July, 2019

Andrei Iancu
*Director of the United States Patent and Trademark Office*